United States Patent [19]

Moguilewsky et al.

[11] Patent Number: 5,276,023
[45] Date of Patent: Jan. 4, 1994

[54] 19-NOR-STEROID ESTERS

[75] Inventors: Martine Moguilewsky, Paris; Lucien Nedelec, Le Raincy; Francois Nique, Pavillons Sous Bois; Daniel Philibert, La Varenne Saint Hilaire, all of France

[73] Assignee: Roussel Uclaf, France

[21] Appl. No.: 876,181

[22] Filed: Apr. 30, 1992

Related U.S. Application Data

[63] Continuation of Ser. No. 563,489, Aug. 7, 1990, abandoned.

[30] Foreign Application Priority Data

Aug. 8, 1989 [FR] France .................. 89 10648

[51] Int. Cl.$^5$ .................. A61K 31/56; A61K 31/58; C07J 17/00
[52] U.S. Cl. .................. 514/179; 552/540; 552/548; 552/553; 552/554; 552/590; 552/643; 552/648
[58] Field of Search .................. 514/179; 552/643, 648, 552/540, 548, 553, 554, 590

[56] References Cited

U.S. PATENT DOCUMENTS

| | | | |
|---|---|---|---|
| 4,396,614 | 8/1983 | Nedelec et al. | 514/179 |
| 4,447,424 | 5/1984 | Teutsch et al. | 514/179 |
| 4,477,445 | 10/1984 | Philibert et al. | 514/172 |
| 4,536,401 | 8/1985 | Neef et al. | 514/173 |
| 4,540,686 | 9/1985 | Philibert et al. | 514/179 |
| 4,609,651 | 9/1986 | Rohde et al. | 514/179 |
| 4,634,695 | 1/1987 | Torelli et al. | 514/178 |
| 4,829,060 | 5/1989 | Ottow et al. | 514/179 |

*Primary Examiner*—Mukund J. Shah
*Assistant Examiner*—Matthew V. Grumbling
*Attorney, Agent, or Firm*—Bierman and Muserlian

[57] ABSTRACT

A compound of the formula

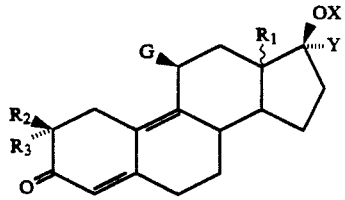

wherein $R_1$ is an aliphatic hydrocarbon of 1 to 8 carbon atoms, $R_2$ and $R_3$ are individually hydrogen or alkyl of 1 to 4 carbon atoms, G is a hydrocarbon of 1 to 18 carbon atoms optionally containing at least one heteroatom and linked to the steroid nucleus by a carbon atom, X is $X_A$ or $X_B$, $X_A$ is selected from the group consisting of hydrogen, alkyl of 1 to 8 carbon atoms, aralkyl of 7 to 15 carbon atoms, acyl of an organic carboxylic acid of 1 to 8 carbon atoms and Y is -B-O—CO—A-Z, B is a saturated or unsaturated, linear or branched alkylene of 1 to 8 carbon atoms, A is a saturated or unsaturated, linear or branched alkylene of 1 to 6 carbon atoms and optionally interrupted or ended by a bivalent aromatic or is a bivalent aromatic and Z is —COOH or —SO$_3$H which may be salified with an alkali metal, alkaline earth metal, an organic amine or —NH$_4$ or $X_B$ is —COAZ, A and Z are defined as above and Y is selected from the group consisting of —C≡C—R$_4$, —CH=CH—R$_4$ and —CH$_2$—CH$_2$—R$_4$, R$_4$ is selected from the group consisting of hydrogen, halogen, alkyl of 1 to 6 carbon atoms, trialkylsilyl having 3 to 12 carbon atoms and phenyl, the alkyl and phenyl being optionally substituted and the 13-wavy line indicates that R$_1$ can be in the $\alpha$- or $\beta$-position having antiprogestomimetic and antiglucocorticoid properties among others.

12 Claims, No Drawings

19-NOR-STEROID ESTERS

PRIOR APPLICATION

This application is a continuation of U.S. patent application Ser. No. 563,489 filed Aug. 7, 1990, now abandoned.

STATE OF THE ART

Related prior art includes U.S. Pat. Nos. 4,829,060 and 4,609,651 and European Patent No. 0,277,676.

OBJECTS OF THE INVENTION

It is an object of the invention to provide the novel compounds of formula I and a novel process and intermediates for their preparation.

It is another object of the invention to provide antiglucocorticoidal and antiprogestomimetic compositions and a method of inducing antiglucocorticoidal and antiprogestomimetic activity in warm-blooded animals.

These and other objects and advantages of the invention will become obvious from the following detailed description.

THE INVENTION

The novel compounds of the invention are compounds of the formula

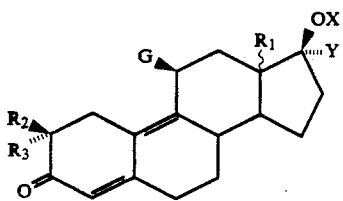

wherein $R_1$ is an aliphatic hydrocarbon of 1 to 8 carbon atoms, $R_2$ and $R_3$ are individually hydrogen or alkyl of 1 to 4 carbon atoms, G is a hydrocarbon of 1 to 18 carbon atoms optionally containing at least one heteroatom and linked to the steroid nucleus by a carbon atom, X is $X_A$ or $X_B$, $X_A$ is selected from the group consisting of hydrogen, alkyl of 1 to 8 carbon atoms, aralkyl of 7 to 15 carbon atoms, acyl of an organic carboxylic acid of 1 to 8 carbon atoms and Y is -B-O—CO—A-Z, B is saturated or unsaturated, linear or branched alkylene of 1 to 8 carbon atoms, A is a saturated or unsaturated, linear or branched alkylene of 1 to 6 carbon atoms and optionally interrupted or ended by a bivalent aromatic or is a bivalent aromatic and Z is —COOH or —SO$_3$H which may be salified with an alkali metal, alkaline earth metal, an organic amine or —NH$_4$ ort $X_B$ is —COAZ, A and Z are defined as above and Y is selected from the group consisting of —C≡C—R$_4$, —CH=CH—R$_4$, —CH$_2$—CH$_2$—R$_4$, R$_4$ is selected from the group consisting of hydrogen, halogen, alkyl of 1 to 6 carbon atoms, trialkylsilyl having 3 to 12 carbon atoms and phenyl, the alkyl and phenyl being optionally substituted and the 13-wavy line indicates that $R_1$ can be in the α- or β-position.

$R_1$ preferably is linear or branched alkyl of one to four carbon atoms such as methyl, ethyl, propyl, isopropyl or butyl. The products in which $R_1$ is in the β-position are preferred.

When $R_2$ or $R_3$ are alkyl, they are preferably methyl but $R_2$ or $R_3$ can equally be ethyl, propyl, isopropyl or butyl.

G notably is either aryl of six to fourteen carbon atoms and optionally substituted by at least one member of the group consisting of halogen, carbamoyl, saturated or unsaturated, branched or linear aliphatic of one to six carbon atoms and optionally substituted by at least one member of the group consisting of halogen, carbamoyl, amino, alkylamino of one to four carbon atoms, dialkylamino of two to eight carbon atoms or a heterocyclic of three to eight links having at least one nitrogen atom and optionally one or two heteroatoms chosen from oxygen or sulfur; linear or branched acyl of one to six carbon atoms; phenoxy optionally substituted by an amino, alkylamino of one to four carbon atoms, dialkylamino of two to eight carbon atoms or by a heterocyclic with three to eight links having at least one nitrogen atom and optionally one or two heteroatoms selected from oxygen or sulfur; phenyl optionally substituted by amino, alkylamino of one to four carbon atoms, dialkylamino of two to eight carbon atoms or a heterocyclic with three to eight links having at least a nitrogen atom and optionally one or two heteroatoms selected from oxygen or sulfur; heterocyclic with three to eight links containing at least one nitrogen atom and optionally one or two heteroatoms selected from sulfur or oxygen and being able themselves to be substituted by one or more alkyls of one to four carbon atoms; alk$_1$alk$_2$N (O)$_m$—, alk$_3$S (O)$_p$— or alk$_4$O— in which alk$_1$, alk$_2$, alk$_3$ and alk$_4$ are individually hydrogen, linear or branched alkyl of one to twelve carbon atoms optionally substituted by amino, alkylamino of one to eleven carbon atoms, dialkylamino of two to eleven carbon atoms, trialkylsilyl of three to eleven carbon atoms or a heterocyclic with three to eight links containing at least a nitrogen atom and optionally one or two heteroatoms selected from sulfur or oxygen atoms and being able itself to be substituted by one or more alkyls of one to four carbon atoms, m is equal to zero or one, and p is equal to zero, one or two; trialkylsilyl of three to twelve carbon atoms; or a saturated or unsaturated, branched or linear aliphatic of one to eighteen carbon atoms and optionally substituted by one or more members of the group consisting of halogen, optionally substituted phenyl, alk$_1$alk$_2$-N(O)$_m$—, alk$_3$S(O)$_p$13 , or alk$_4$O— in which alk$_1$, alk$_2$,alk$_3$, alk$_4$, m and p are as defined previously; heterocyclic with three to eight links containing at least one nitrogen atom and optionally one or two heteroatoms selected from sulfur or oxygen atoms and being able itself to be substituted by one or more alkyls of one to four carbon atoms; trialkylsilyl of three to twelve carbon atoms; or a heterocyclic optionally substituted by at least one member of the group consisting of halogen, linear or branched alkyls of one to six carbon atoms and optionally substituted by carbamoyl, amino, alkylamino of one to four carbon atoms, dialkylamino of two to eight carbon atoms or a heterocyclic with three to eight links having at least one nitrogen atom and optionally one or two heteroatoms selected from oxygen or sulfur atoms, alk$_1$alk$_2$N(O)$_m$—, alk$_3$S(O)$_p$— or alk$_4$O— in which alk$_1$, alk$_2$, alk$_3$, alk$_4$, m and p are as defined previously; trialkylsilyl of three to twelve carbon atoms, or a condensed bicyclic system containing one to three nitrogen atoms and of which one is optionally oxidized, optionally substituted by one or more members of the group consisting of halogen or alkyl of one to four carbon atoms;

or a cycloalkyl of three to eight links and optionally substituted by one or more members of the group consisting of halogen, phenyl, linear or branched alkyls of one to six carbon atoms and optionally substituted by carbamoyl, amino, alkylamino of one to four carbon atoms, dialkylamino of two to eight carbon atoms or a heterocyclic with three to eight links having at least one nitrogen atom and optionally one or two heteroatoms chosen from oxygen or sulfur atoms; $alk_1alk_2N(O)_m-$, $alk_3S(O)_p$ or $alk_4O-$ in which $alk_1$, $alk_2$, $alk_3$, $alk_4$, m and p are as defined previously; and trialkysilyl of three to twelve carbon atoms.

Preferably, G can be aryl which may be substituted in ortho, meta or para position by one or more alkyls of preferably 1 to 4 carbon atoms; by one or more alkoxys of preferably 1 to 4 carbon atoms such as methoxy, ethoxy, propoxy, isopropoxy, butoxy, isobutoxy, tert.-butoxy; alkenyloxy such as vinyloxy or 2-propenyloxy; by one or more halogens, preferably chlorine or fluorine; by one or more of the following groups hydroxyl, (2-amino-2-oxoethyl), trifluoromethyl, alkylthio of 1 to 4 carbon atoms optionally oxidized in the form of sulfoxide or sulfone such as methyl thio, ethylthio; amino, alkylamino of one to four carbon atoms such as methylamino, ethylamino, dialkylamino of two to eight carbon atoms optionally oxidized in the form of N-oxide such as dimethylamino, diethylamino or (N-methylethylamino), by an acyl such as formyl, acetyl, propionyl, butyryl or benzoyl, preferably acetyl; it being understood that the radicals substituting the aryl radical can also be optionally substituted as described previously; similarly, the aryl can be substituted by a combination of these different substituents such as for example (3-fluoro-4-dimethylaminophenyl);

G may also be a heterocyclic optionally substituted by the different radicals envisaged above. The following heterocycles can be cited; thienyl, furyl, isothienyl, isofuryl, thiazolyl, isothiazolyl, oxazolyl, isoxazolyl, thiadiazolyl, pyridyl, piperidinyl or pyrrolidinyl or piperazinyl and heterocycles known to a man of the art;

G may also be a condensed bicyclic comprising a phenyl nucleus and a heterocyclic nucleus containing at least one nitrogen atom optionally substituted by the groups envisaged previously such as N-methyl-2,3-dihydro-indol-5-yl;

G may also be cycloalkyl such as cyclopropyl, cyclobutyl, cyclopentyl or cyclohexyl, cycloalkenyl such as cyclobutenyl or cyclopropenyl;

G may also be an aryl nucleus substituted either by an amine function optionally substituted by one or two alkyls of 1 to 8 carbon atoms, or by an amino incorporated in a heteocycle option ally containing another heteroatom chosen from the group formed by oxygen, nitrogen and sulfur such as morpholino, piperidinyl, pyrrolidinyl or 4-methyl piperazinyl. The aryl nucleus is preferably the phenyl nucleus.

As substituents on the aryl nucleus, an amino (substituted) alkyl can also be envisaged such as dimethylamino methyl, dimethylamino ethyl; an amino (substituted) alkoxy such as dimethylamino ethoxy.

Groups having a silicon can also be cited such as trimethyl silyl phenyl or [N-methyl-(1-trimethylsilyl)-methylamino]-phenyl. The groups comprising a nitrogen atom can be oxidized. G may also be a saturated or unsaturated, linear or branched alkyl of 1 to 18 carbon atoms.

Therefore, examples of suitable groups are methyl, ethyl, propyl, isopropyl, butyl,isobutyl or tert.-butyl,n-pentyl, n-hexyl, 2-methyl pentyl, 2,3-dimethyl butyl, n-heptyl, 2-methylhexyl, 2,2-ddimethylpentyl, 3,3-dimethyl pentyl, 3-ethylpentyl, n-octyl, 2,2-dimethylhexyl, 3,3-dimethylhexyl, 3-methyl-3-ethylpentyl, nonyl, 2,4-dimethyl heptyl, or n-decyl. There can also be cited the vinyl, isopropenyl, allyl, 2-methylallyl or isobutenyl.

The previously cited radicals can be substituted with such possible substituents as thioalkyl like thiomethyl or thioethyl; G can also be substituted by one or more halogens such as fluorine, chlorine, bromine, iodine, or by the substituted amino such as dimethylamino. In a general manner, the products in which G comprises a heteroatom, preferably nitrogen, oxygen or sulfur, are preferred.

When X is $X_A$ and is alkyl, it is preferably methyl, ethyl or propyl. When X is $X_A$ and is an arylalkyl, it is preferably benzyl or phenethyl. When X is $X_A$ and is an acyl, it is preferably formyl, acetyl, propionyl, butyryl or benzoyl.

B preferably is either a saturated bivalent such as methylene, ethylene, trimethylene or tetramethylene, or an unsaturated bivalent such as vinylene, propenylene, butenylene, ethynylene, propynylene or butynylene.

A preferably is methylene, ethylene, trimethylene or tetramethylene and when it is interrupted by an aromatic ring, A therefore preferably is

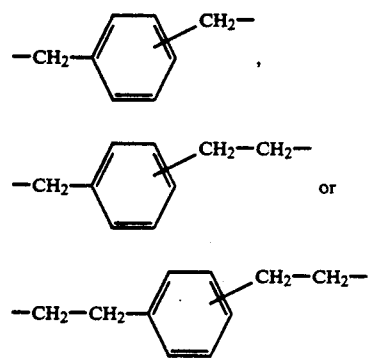

when it is completed by an aromatic ring, it is preferably

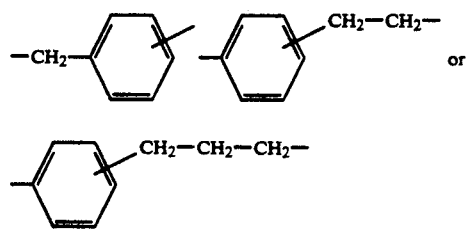

Then A is a bivalent aromatic, it is preferably orthophenylene, metaphenylene or paraphenylene or also

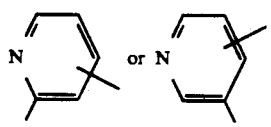

When Z is a salified carboxy or sulfo, it is preferably the salt of sodium, potassium, calcium, magnesium, ammonium, or an amino salt such as the salts of lysine, arginine, cyctene, betaine carnitine, meglumine, quinine, sarcosine, procaine, histidine or N-methyl glucamine.

When $R_4$ is alkyl, it is preferably methyl, ethyl, propyl,

When $R_4$ is alkyl, it is preferably methyl, ethyl, propyl, butyl, isopropyl or isobutyl.

A preferred group of compounds of the invention are those of the formula (I')

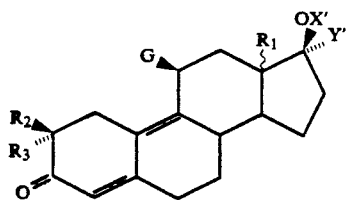

wherein X' is hydrogen and Y' is $Y'_A$, $Y'_A$ being

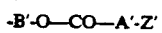

in which B' is one of —CH═CH—CH₂ or C≡C—CH₂—, A' is —(CH₂)ₙ— in which n is two to six or an ortho-, meta- or para- phenylene and Z' is carboxy or sulfo functions or their sodium salt, or X' is $X'_B$, $X'_B$ being

in which n and Z' are as defined previously and Y' is $Y'_B$, $Y'_B$ being —C≡C—R'₄ or —CH═CH—R'₄ in which R'₄ is hydrogen, halogen, trimethyl silyl, or methyl optionally substituted by one or more halogen, hydroxy or alkoxy, alkylthio or alkylamino of one to four carbon atoms, dialkylamino of two to eight carbon atoms or trialkylsilyl of three to twelve carbon atoms.

n preferably is two to four; when R'₄ is trialkylsilyl, it is preferably trimethylsilyl.2 When R'₄ is optionally substituted methyl, it is preferably one of the following; fluoromethyl, trifluoromethyl, chloromethyl, bromomethyl, dimethylaminomethyl, hydroxymethyl, methoxymethyl or methylthiomethyl. When R'₄ is halogen, it is preferably chlorine, bromine or iodine.

More precisely, G is aryl substituted by halogen, aryl, acyl of one to eight carbon atoms, or —NH₂, —NHR' or —NR'R", in which R' and R" are individually phenyl, or primary, secondary or tertiary alkyl of 1 to 8 carbon atoms optionally containing one or more heteroatoms chosen from oxygen, nitrogen and sulfur, or optionally substituted by a heterocycle, or R' and R" together with the nitrogen to which they are linked form a heterocyclic optionally substituted and optionally containing another heteroatom chosen from nitrogen, oxygen and sulfur or —OR'" or —SR'" functions in which R'" is phenyl or primary, secondary or tertiaryl alkyl of one to 8 carbon atoms optionally containing one or more heteoatoms chosen from oxygen, nitrogen, sulfur or optionally substituted by a heterocycle, or G is 2-, 3- or 4-pyridyl.

More preferred products of formula I and I' as defined previously are those in which G is phenyl substituted in position 4 by one of the following: amino, methylamino, dimethylamino or its N-oxide, diethylamino, dipropylamino, N-methyl ethylamine, N-methyl isopropylamino, N-methyl isobutylamino, N-methyl isopentylamino, 1-pyrrolidinyl, [2-(dimethylamino)-N-methyl ethylamino], [N-methyl-2-(1-pyrrolidinyl)-ethylamino], [N-methyl-2-(4-morpholinyl)-ethylamino], (4-methyl-1-piperazinyl); formyl, acetyl, methoxy, phenoxy, [2-(dimethylamino)-ethoxy], [2-(1-pyrrolidinyl)-ethoxy], [2-(4-morpholinyl)-ethoxy], methylthio, ethylthio, isopentylthio, [2-(dimethylamino)-ethylthio], [2-(1-pyrrolidinyl)-ethylthio], [2-(4-morpholinyl)-ethylthio], trimethylsilyl, methyl, isopropyl, [(dimethylamino)-methyl], or by one of fluorine, chlorine or bromine and those wherein $R_1$ is methyl in the 13-position and $R_2$ and $R_3$ each are hydrogen.

Specific preferred compounds of the invention are sodium and 21-chloro-11β-[4-dimethylamino-phenyl]-19-nor-17α-Δ⁴,⁹-pregnadien-3-one-20-yn-17β-yl succinate, sodium and 11β-[4-methylthio-phenyl]-17α-(1-propynyl)-Δ⁴,⁹-estradien-3-one-17β-yl succinate, and 11β-[4-dimethylaminophenyl]-17α-(1-propynyl)-Δ⁴,⁹-estradien-3-one-17β-yl acid succinate and its sodium salt.

The novel process of the invention for the preparation of the compounds of formula I comprises reacting a compound of the formula

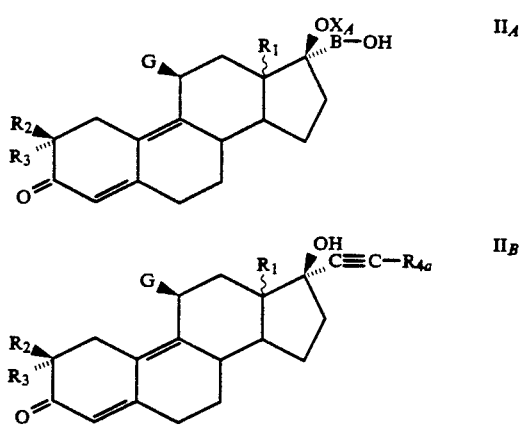

in which $X_A$, $R_1$, $R_2$, $R_3$ and G have the above meanings and $R_{4a}$ has the values indicated above for $R_4$ as well as those values in which the reactive functions are protected in a neutral solvent and in the presence of a base with a) a product of the formula

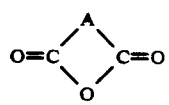

to obtain after, if necessary, deprotection of the protected reactive functions and, if desired, salification of the carboxy function the compounds respectively of the formula

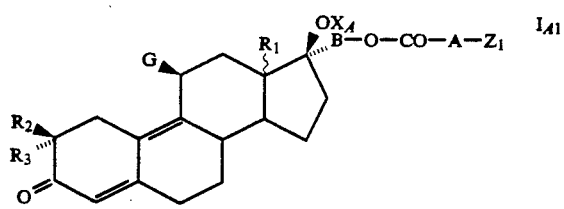

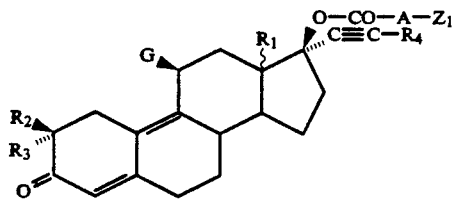

in which $Z_1$ is optionally salified carboxy or b) a product of the formula

HOOC—A-U  III or also a functional derivative thereof in which U is —COOH, —COOR$_5$ in which R$_5$ is alkyl of one to six carbon atoms or arylalkyl of seven to twelve carbon atoms, or —SH to obtain after, if necessary deprotection of the protected reactive functions, products of the formulae respectively:

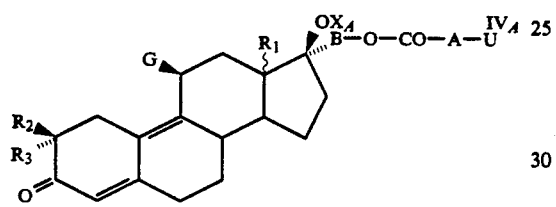

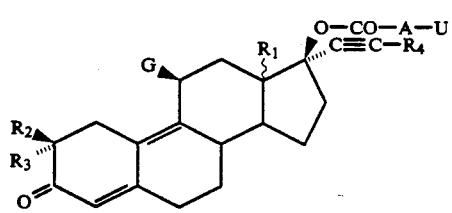

which products when U is free carboxy, correspond, after optional salification, to products of formulae $I_{A1}$ and $I_{B1}$ and when U is —COOR$_5$, correspond to the products of the formula

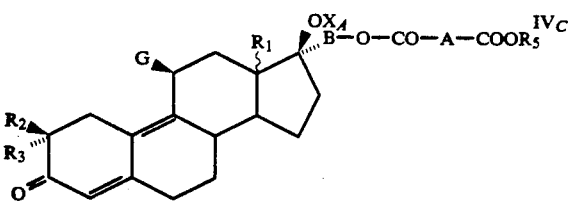

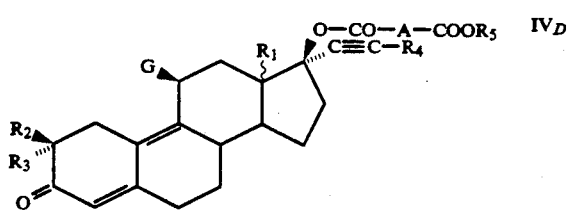

which products are hydrolyzed or saponified to obtain the products of formulae $I_{A1}$ and $I_{B1}$ respectively, and when U is —SH, correspond to products of the formulae

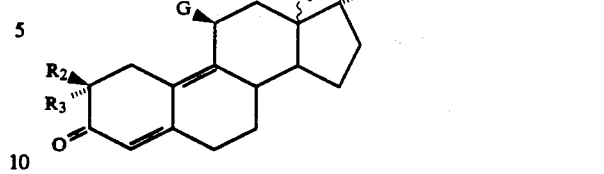

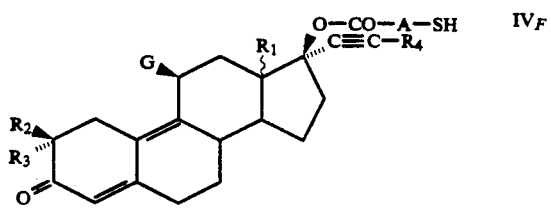

which products are oxidized and if desired salified to obtain the products corresponding to the formulae respectively:

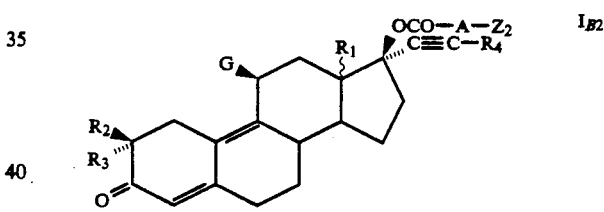

in which $Z_2$ is optionally salified sulfo or c) product of the formula

HOOC—A—SO$_2$Cl  III$_3$ or also a functional derivative thereof to obtain if necessary after deprotection of reactive functions contained in R$_{4B}$ and if desired after salification, products of formula $I_{A2}$ and $I_{B2}$ respectively; and in that:

B— the products of formula $I_{B1}$, $I_{B2}$ and IV$_D$ are subjected if desired:

a) either to a hydrogenation agent of the triple bonds to obtain the products of the formulae respectively:

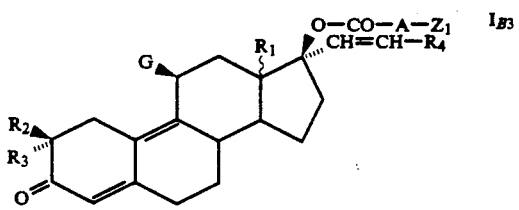

-continued

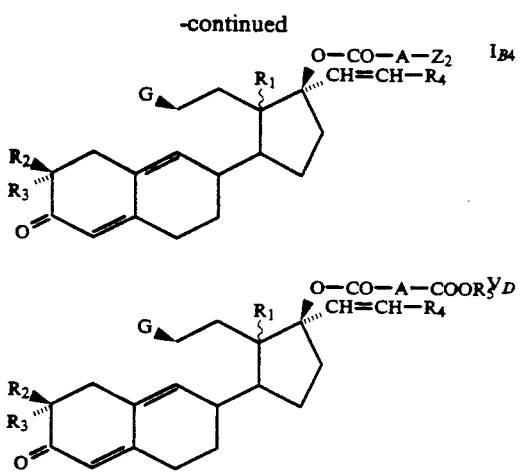

and, if desired, subjecting the latter to a hydrogenation agent of the double bonds to obtain products of the formulae, respectively:

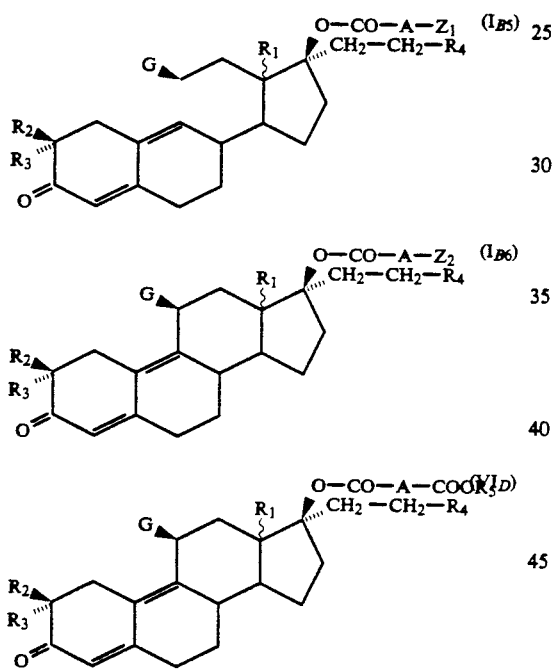

or to an agent for direct hydrogenation of the triple bonds into single bonds to obtain the products of formulae $I_{B5}$, $I_{B6}$ and $VI_D$, respectively.

b) the products of formulae $V_D$ and $VI_D$ are either hydrolyzed, or saponified to obtain the products of formulae $I_{B3}$ and $I_{B5}$, respectively.

In a preferred embodiment of the process, the reaction of $III_1$ with $II_A$ and $II_B$ is effected in the presence of a base and in a neutral solvent, the hydroxy function optionally contained in $R_4$ being protected in the form of a (2-tetrahydropyrannyloxy). The subsequent deprotection of this function takes place by passage over commercial sulfonic resin (acid form) or by acidic treatment. The neutral solvent serving as the reaction medium can be chloroform, methylene chloride, acetonitrile or ethyl ether and the base used is preferably a nitrogenous base such as triethylamine, diisopropylethylamine, 4-dimethylaminopyridine, pyridine or N-methyl morpholine.

The oxidation of the mercapto group into the sulfo group is effected with nitric acid, barium nitrate or by auto-oxidation in a basic medium. The agent for hydrogenation of the triple bond into the bond double is hydrogen in the presence of a catalyst such as palladium on barium sulfate. The agent for hydrogenation of the double or triple bonds into a single bond is hydrogen in the presence of a catalyst such as palladium on activated charcoal or rhodium chloro-tris-(triphenylphosphine).

By functional derivatives of the acids of formula $III_2$ or $III_3$, is meant the anhydrides obtained "in situ" by action of an alkyl chloroformate such as isobutyl chloroformate, or a dicycloalkylcarbodiimide such as dicyclohexylcarbodiimide. The hydrolysis and saponification of the $-COOR_5$ function, as well as the salification of the carboxy or sulfo functions, is carried out in the usual way.

In a preferred embodiment of the process for the preparation of the products of formula I', a) either the product of the formula

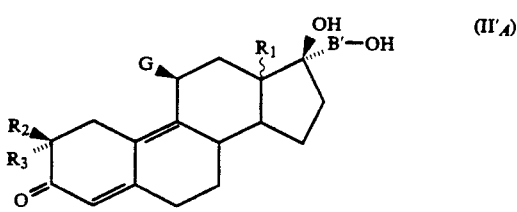

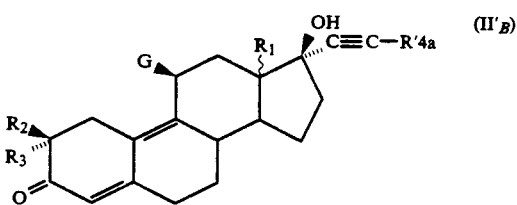

in which $R_1$, $R_2$, $R_3$ and G have the above definition and $R'_{4B}$ has values of $R'_4$ as well as those values in which the hydroxylated functions are protected in a neutral solvent and in the presence of a base is reacted with a product of the formula

in which n is two to six to obtain, if necessary after deprotection of the protected hydroxy function contained in $R'_4$ and if desired, after salification of the free carboxy function by the action of a solution of sodium bicarbonate, the product of the formula respectively:

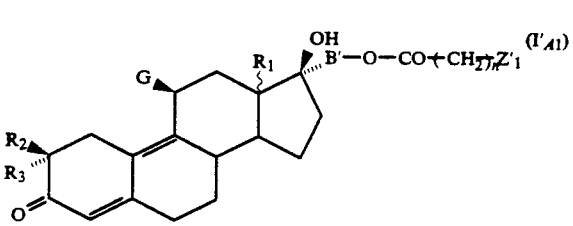

-continued

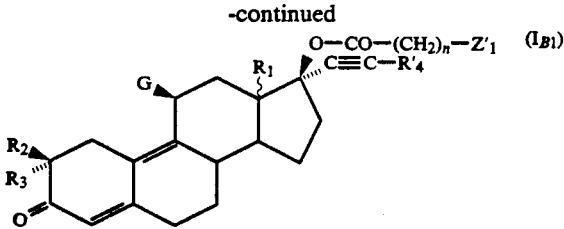

in which $Z'_1$ is free carboxy or its sodium salt, b) or the product of formula $II'_A$ is reacted in the presence of a nitrogenous base with a product of the formula

to obtain, if necessary and if desired, after salification by a solution of sodium bicarbonate, a product of the formula

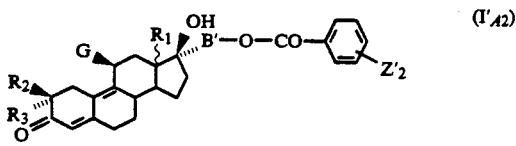

in which $Z'_2$ is sulfo or its sodium salt, which products of formula $I'_{B1}$ if desired, are subjected to the action of hydrogen in the presence of a catalyst to obtain the products of the formula

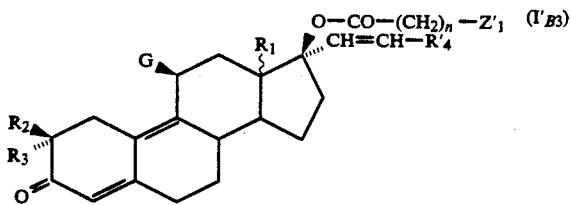

The products formulae $II_A$ and $II_B$ used as starting materials are generally known and their preparations are described in French Patent No. 2,377,418; No. 2,497,807; No. 2,522,328; No. 2,528,434 and European Patent No. 057,115 and No. 190,759.

Some of the products of formulae $III_1$, $III_2$ and $III_3$ are commercially available products and the others can be prepared by known methods such as:

ETAIX, annales de Chemie (7) Vol. 9 p. 371
LOVEN, J. Prakt. Chemie (2) Vol. 29 p. 376
UHLENBROEK, Recueil des Travaux Chimiques des Pays-Bas (1957) Vol. 76 p. 129, 142.

The compounds of formula I possess progestomimetic or antiprogestomimetic, androgenic or antiandrogenic activities as well as glucocorticoid and/or antiglucocorticoidal, antiproliferative and antiestrogenic and/or estrogenic activity.

The compounds are useful for combatting the secondary effects of glucocorticoids and also allow the combatting of disorders due to a hypersecretion of glucocorticoids and especially against aging in general and more particularly against hypertension, glaucoma, atherosclerosis, osteoporosis, diabetes, obesity as well as immuno depression and insomnia.

The products which possess antiprogestomimetic properties can be used to prepare original contraceptives or as agents for interrupting pregnancy. The products are also useful as inducers of womens' periods and more generally for warm-blooded female animals.

These products are administered during periods where progesterone plays an essential physiological role, or during the luteal phase of the cycle, at the moment of nidation (or implantation of the embryo) and during pregnancy. A method of contraception of the invention consists of administering to women at least one of the compounds of formula I over 1 to 5 days preferably situated at the end of the cycle. These products are then preferably administered orally or in vagino but they can also be used parenterally. The products may also be used by endonasal route.

The products possessing antiprogestomimetic properties can also be used against hormonal disturbances and, furthermore, they can be useful in the treatment of hormono-dependent tumors. Their action on hypophysial secretions make the products useful for menopause. The products can equally be used in the synchronization of estrus in farm animals, especially cattle and sheep as well as to control the fertility of domestic animals such as dogs or cats.

The products may also present progestomimetic properties and can thus be used in the treatment of amenorrheas, dysmenorrheas and luteal insufficiencies.

The products that present anti-androgen properties can be used in the treatment of hypertrophia and cancer of the prostate, virilism, anaemia, hirsutism and acne as well as for male contraception.

Finally, the products that present anti-proliferative, anti-estrogen and/or estrogen properties can be used in the treatment of hormono-dependent carcinomas such as mammary carcinomas and their metastases. These properties also render the products useful in the treatment of benign breast tumors. The estrogen properties make them usable in the treatment of disorders linked to a hypofolliculinemia, for example amenorrheas, dysmenorrheas, repeated abortions, premenstrual disorders as well as treatment for the menopause.

The novel antiglucocorticoid and antiprogestomimetic compositions of the invention are comprised of an effective amount of at least one compound of formula I and their non toxic pharmaceutically acceptable salts and an inert pharmaceutical carrier or excipient.

The pharmaceutical compositions may be in the form of tablets, dragees, capsules, granules, suppositories, vaginal suppositories, injectable preparations, ointments, creams, gels prepared in the usual methods.

Examples of excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The novel method of the invention for inducing antiglucocorticoid and antiprogestomimetic activity in warm-blooded animals, including humans, comprises administering to warm-blooded animals an effective amount of at least one compound of Formula I and their non-toxic, pharmaceutically acceptable salts. The usual daily dosage is 0.15 to 13.33 mg/kg depending on the method of administration, the specific compound and the condition being treated. The compounds may be administered orally, rectally, parenterally or topically.

Moreover, the products of formula I in which Z is a salified carboxy or salified sulfo and especially the products of formula I' in which Z' is —COONa or —SO$_3$Na, are very soluble in water. For example, the solubility of the product of Example 18 is greater than 25 g for 100 ml of water which allows their use in the form of drinkable, nasal or auricular solutes, collyria, aerosols, IM or IV injectable solutions or capsules.

When the active compound to be administered is an antiglucocorticoid or an antiprogestomimetic, the preferred compounds are the compounds of Examples 5, 6, 10 and 12 and the usual oral dosages is 1.3 to 13.3 mg/kg.

The novel intermediates of the invention are the compounds of formulae IV$_C$, IV$_D$, IV$_E$, IV$_F$, V$_D$ and VI$_D$.

In the following examples there are described several preferred embodiments to illustrate the invention. However, it is to be understood that the invention is not intended to be limited to the specific embodiments.

EXAMPLE 1

(Z)-3-[11β-[4-dimethylamino-phenyl]-Δ$^{4,9}$-estradien-17β-ol-3-one-17α-yl]-2-propenyl acid succinate 900 mg of 11β-[4-dimethylamino-phenyl]-17α-[(Z)-3-hydroxy-1 propenyl]-Δ$^{4,9}$-estradien-17β-ol-3-one were dissolved in 9 ml of chloroform in a flask provided with a magnetic stirrer and, then 304 mg of succinic anhydride and 1.45 ml of triethylamine were added. The mixture was stirred for 15 hours at ambient temperature and then evaporated to dryness. The 1.443 g of residue were purified by chromatography on a column of silica (eluant: (ethyl acetate 90-cyclohexane 10)-acetic acid 3%). After recrystallization from a methanol water mixture (60-40), 695 mg of the desired product in the form of yellow crystals melting at approx. 145° C. were obtained. Thin layer chromatography: Rf=0.60. support: KC 18 Whatman ®, eluant: methanol-aqueous 0.05 molar ammonium acetate solution (80-20)).

EXAMPLE 2

Sodium (Z)-3-[11β-[4-dimethylamino-phenyl]-Δ$^{4,9}$-estradien-17β-ol-3-one-17α-yl]-2-propenyl succinate 93 mg of sodium bicarbonate were dissolved in 20 ml of water in a flask provided with a magnetic stirrer and a solution of 639 mg of the product of Example 1 in 20 ml of ethanol were then added dropwise. The ethanol was eliminated by azeotropy and the aqueous solution was filtered on Millipore ® membrane (0.45 micron), then lyophilized to obtain. 654 mg of the desired product in the form of a cream-colored powder with a specific rotation of [α]$_D$=+101°±2° (c=1% in water). Thin layer chromatography: Rf=0.62. (support: KC 18 Whatman ®, eluant: methanol - aqueous 0.05 molar solution of ammonium acetate (80-20)).

EXAMPLE 3

3-[11β-[4-dimethylamino-phenyl-]Δ$^{4,9}$-estradien-17β-ol-3-one-17α-yl]-2-propynyl acid succinate 900 mg of 11β-[4-dimethylamino-phenyl]-17α-(3-hydroxy-1-propynyl)-Δ$^{4,9}$-estradien-17β-ol-3-one were dissolved in 9 ml of chloroform in a flask provided with a magnetic stirrer and 303 mg of succinic anhydride and 1.4 ml of triethylamine were then added. The mixture was stirred for 17 hours at ambient temperature and after evaporation to dryness, 1.685 g of crude product were purified by chromatography on a Bondapack C18 ® column (eluting with a mixture of methanol and aqueous 0.05 molar solution of ammonium acetate (60-40)) to obtain 1.104 g of the desired product with an Rf=0.63 (thin layer chromatography, support: KC 18 Whatman ® eluant: methanol-aqueous 0.05 molar solution of ammonium acetate (80-20)).

EXAMPLE 4

Sodium and 3-[11β-[4-dimethylamino-phenyl]-Δ$^{4,9}$-estradien-17β-ol-3-one-17α-yl]-2-propynyl succinate Using the procedure of Example 2, 141 mg of sodium bicarbonate in 29 ml of water and 964 mg of the product of Example 3 in 29 ml of ethanol were reacted to obtain 935 mg of the sought product with a specific rotation of [α]$_D$=+55°±1,5° (c=1% water) and a Rf=0.63 (thin layer chromatography, support: KC 18 Whatman ®, eluant: methanol -aqueous 0.05 molar solution of ammonium acetate (80-20)).

EXAMPLE 5

11β-[4-dimethylamino-phenyl]-17-(1-propynyl)-Δ$^{4,9}$-estradien-3-one-17β-yl acid succinate The reaction medium was prepared by adding 2.15 g of succinic anhydride, 2.2 ml of triethylamine and 215 mg of 4-dimethylamino pyridine to a solution of 2.15 g of 11β-[4-dimethylamino-phenyl]-17α-(1-propynyl)-Δ$^{4,9}$-estradien-17 β-ol-3-one in 22 ml of chloroform. The mixture was refluxed for 42 hours and 430 mg of 4-dimethyl-amino-pyridine and 4.4 ml of triethylamine were added. Reflux was continued for 26 hours and the solution was then poured into a water - ice mixture. After decantation of the organic phase, it was washed with water, then dried and the chloroform was distilled off to give a dry brown-colored extract. The aqueous phase was acidified with 0.5N hydrochloric acid, then neutralized by the addition of sodium acetate. Extraction was carried out again with ethyl acetate and the new organic phase was washed with water, dried and after distillation of the solvent a residue resulted that was combined with the previous one. The product was purified on a silica column with elution with an ether - ethyl acetate mixture (9-1) with 3% acetic acid. The product was crystallized twice from an ether - methylene chloride mixture to obtain 1.435 g of the sought product melting at approx. 165° and having a specific rotation of [α]$_D$=+97° (c=0.8% in CHCl$_3$) and a Rf=approx. 0.40 (thin layer chromatography, support: SiO$_2$, eluant: ether - ethyl acetate (9-1) - 3% acetic acid).

EXAMPLE 6

Sodium 11β-[4-dimethylamino-phenyl]17α-(1-propynyl)-Δ$^{4,9}$-estradien-3-one-17β-yl succinate 3 g of the product of Example 5 and 94 ml of ethanol were introduced into a flask provided with a magnetic stirrer and a solution of 433 mg of sodium bicarbonate in 94 ml of water was then poured in. After 30 minutes of stirring at ambient temperature, the ethanol was eliminated by azeotropy and the remaining solution was filtered on Millipore ® membrane (0.45 microns) and lyophilized to obtain 2.88 g of the sought product with a specific rotation of [α]$_D$=+48.50±1.50 (c=1% in water) and a Rf=0.54 (thin layer chromatography, support: KC 18 Whatman ®, eluant: methanol - aqueous 0.05 molar solution of ammonium acetate (80-20)).

EXAMPLE 7

11β-[4-dimethylamino-phenyl]-17α-[(Z)-1-propenyl-Δ$^{4,9}$-estradien-3-one-17β-yl acid succinate 2.462 g of the product of Example 5 were put into a flask provided with a magnetic stirrer and 150 ml of ethyl acetate with 2% pyridine, 15 ml of water and 50 mg of 10% palladium hydroxide on barium sulfate were added. After hydrogenation with stirring for five and a half hours, the reaction medium was filtered and the pyridine was eliminated. The remaining solution was evaporated to dryness and the residue was purified twice in succession by chromatography on a Bondapack C 18 column eluting with a mixture of methanol - aqueous 0.05 molar solution of ammonium acetate (65-35) to obtain 576 mg of the sought product with a Rf=0.50 (thin layer chromatography; support: KC 18 Whatman ® eluant: methanol - aqueous 0.05 molar solution of ammonium acetate (80-20)).

EXAMPLE 8

Sodium and 11-62 -8 4-dimethylamino-phenyl]-17α-[(Z)-1-propenyl]-Δ$^{4,9}$-estradien-3-one-17β-yl succinate Using the procedure of Example 2, a solution of 100 mg of sodium bicarbonate in 21 ml of water and 665 mg of the product of Example 7 in 21 ml of ethanol were reacted to obtain 583 mg of the sought product with a specific rotation of $[α]_D= +56.5° ± 1.5°$ (c=1% in water) and a Rf=0.50 (thin layer chromatography, support KC 18 Whatman ® eluant: methanol - aqueous 0.50 molar solution of ammonium acetate (80-20)).

EXAMPLE 9

21-chloro-11β-[4-dimethylamino-phenyl]-19-nor-17α-Δ$^{4,9}$-pregnadien-3-one-20-yn-17β-yl acid succinate 1.854 g of 21-chloro-11β-[4-dimethylamino-phenyl]-17α-Δ$^{4,9}$-pregnadien-17β-ol-20-yn-3-one were dissolved in 18.5 ml of chloroform in a flask provided with a magnetic stirrer and then 2,497 g of succinic anhydride, 7 ml of triethylamine and 0.936 g of 4-(dimethylamino)-pyridine were added. The mixture was refluxed or 42 hours and the reaction was then poured into 31 ml of a 2N hydrochloric acid solution. Then, the pH was adjusted to 6-7 by the addition of sodium acetate and the chloroform phase was extracted twice with chloroform. The collected extracts were united, washed with water, dried on sodium sulfate and then concentrated under reduced pressure to obtain 3.85 g of a brown residue which was purified by chromatography on a column of Kieselgel, eluting first with ethyl ether then with an ethyl ether and 3% acetic acid mixture to obtain 1.8 g of crude product. The latter was crystallized from a methylene chloride-ethyl ether mixture, then from a methylene chloride-ethyl ether mixture to obtain 1.21 g of the expected product with a melting point of approx. 165° C. and a specific rotation of $[α]_D= +63° ± 1.5°$ (c=0.90 in CHCl$_3$). Thin layer chromatography: Rf=0.53. (support: KC 18 Whatman ®; eluant: methanol - aqueous 0.05 molar solution of ammonium acetate (80-20)).

EXAMPLE 10

Sodium and 21-chloro-11β-[4-dimethylamino-phenyl]-19-nor-17α-Δ$^{4,9}$-pregnadien-3-one-20-yn-17β-yl succinate 817 mg of the product of Example 9 and 25 ml of ethanol were mixed together in a flask provided with a magnetic stirrer and a solution of 113 mg of sodium bicarbonate in 25 ml of water was added dropwise. The reaction medium was stirred for 30 minutes at ambient temperature and the ethanol was eliminated by azeotropy. The remaining solution was filtered on Millipore ® membrane (0.45 microns), then lyophilized to obtain 813 mg of lyophilizate which correspond to the sought product with a specific rotation of $[α]_D= +16.5° ± 1°$ (c=1% in H$_2$O). Rf=0.54 (thin layer chromatography; support: KC 18 Whatman ® eluant: methanol - aqueous 0.05 molar solution of ammonium acetate (80-20)).

EXAMPLE 11

11β-[4-methylthio-phenyl]-17α-(1-propynyl)-Δ$^{4,9}$-estradien-3-one-17β-yl acid succinate 1.5 g of 11β-[4-methylthio-phenyl]-17α-(1-propynyl-Δ$^{4,9}$-estradien-17β-ol-3one and 15.3 ml of chloroform were mixed together in a flask provided with a magnetic stirrer and a cooling agent, and then 1.86 g of succinic anhydride, 6 ml of triethylamine and 794 mg of 4-(dimethylamino)-pyridine were added. The mixture was refluxed for 94 hours and then poured into 1N hydrochloric acid and extracted with chloroform. The chloroform phase was washed with water, dried on sodium sulfate and the solvent was eliminated under reduced pressure at 40° C. to obtain 2.26 g of crude product which was chromatographed on a 60H Kieselgel ® silica column (eluant: (methylene chloride 97.5 - methanol 2.5 - acetic acid 1%). After crystallization from a methylene chloride - isopropyl ether mixture 826 mg of crystals of the sought product melting at 158° C. were obtained. Rf=0.61 (thin layer chromatography, support KC 18 Whatman ® eluant: mixture of ethanol and aqueous 0.05 molar solution of ammonium acetate (70-30)).

EXAMPLE 12

Sodium and 11β-[4-methylthio-phenyl]-17α-(1-propynyl)-Δ$^{4,9}$estradien-3-one-17β-yl succinate Using the procedure of Example 2, 108 mg of sodium bicarbonate in 21.5 ml of water and 719 mg of the product of Example 11 in 21.5 ml of ethanol were reacted to obtain 720 mg of a lyophilizate corresponding to the sought product with a specific rotation of $[α]_D= +74.5° ± 1.5°$ (c=1% in water). Rf=0.61 (thin layer chromatography, support KC 18 Whatman ® eluant: ethanol - aqueous 0.05 molar solution of ammonium acetate (70-30)).

EXAMPLE 13

3-[3-[11β-[4-dimethylamino-phenyl]-Δ$^{4,9}$-estradien-17β-ol-3-one-17α-yl]-2-propynyloxy-carboxyl]-benzenesulfonic acid 1 g of 11β-[4-dimethylamino-phenyl]-17α-(3-hydroxy-1-propynyl)-Δ$^{4,9}$-estradien-17β-ol-3-one was dissolved in 10 ml of chloroform and 1.5 g of the pyridine-3-(chlorosulfonyl)-benzoic acid complex, then 1.25 ml of triethylamine were added. The mixture was refluxed for 45 minutes and after another 0.5 g of the previous complex were added, reflux was continued for 30 minutes. After cooling, the solvent was evaporated off and the residue was dissolved in water. Then, the solution was distilled in the presence of toluene and the dry extract was dissolved in chloroform and filtered on a column of silica. Elution with chloroform with 5% ethanol, then with chloroform with 10% ethanol yielded an acid fraction from which 1.7 g of the sought product was isolated in the form of a pale yellow resin.

EXAMPLE 14

Sodium 3-[3-[11β-[4-dimethylamino-phenyl]-Δ$^{4,9}$-estradien-17β-ol-3-one-17α-yl]-2-propynyloxycarbonyl]-benzenesulfonate 25 ml of an ethanol solution of sodium acetate (0.24 mmole/ml) were added to the acid fraction obtained in Example 13 and the solution was evaporated to dryness. The dry extract was taken up in methanol with 33% water and chromatrographed on a LICHROSORB KC 18 ® (eluents: methanol - water (3-6), methanol - water (1-1) then methanol - water (6-3)). The eluants were refiltered, evaporated to dryness and the powder obtained was dried to obtain 1.35 g of the sought product with a specific rotation of $[\alpha]_D = +107°$ (c=0.2% in ethanol).

| Analysis: | | | | |
|---|---|---|---|---|
| Calculated: | % C 66.34 | % H 5.87 | % N 2.25 | % S 4.92 |
| Found: | 66.6 | 6.30 | 2.50 | 4.7 |

EXAMPLE 15

11β-(4-acetyl-phenyl)-17α-(1propynyl)-Δ$^{4,9}$-estradien-3-one-17β-yl acid succinate 1.8 g of 11β-(4-acetyl-phenyl)-17α-(1-propynyl)-Δ$^{4,9}$-estradien-17β-ol-3-one were dissolved in 18 ml of chloroform and then 2.54 g of succinic anhydride, 7 ml of triethylamine and 0.95 g of 4-dimethylamino pyridine were added. The solution was refluxed for 70 hours and after cooling to ambient temperature, the reaction medium was poured into 2N hydrochloric acid and extracted with chloroform. The organic phase was washed with water, dried on sodium sulfate and evaporated to dryness under vacuum. The crude product was chromatographed on a Kieselgel 60 ® silica column, eluting first with ethyl ether, then with ethyl ether with 3% acetic acid to obtain 1.37 g of crude product which was purified by crystallization from a mixture of methylene chloride and ethyl ether then crystallization from an identical mixture to obtain 1.027 g of sought product melting at approx. 168° C. and with a Rf=0.32 (then layer chromatography; support: SiO$_2$F$_{254}$ Merck 60 ® eluant: mixture of ethyl ether - ethyl with 3% acetic acid (90-10)).

EXAMPLE 16

Sodium and 11β-(4-acetyl-phenyl)-17α-(1-propynyl)-Δ$^{4,9}$-estradien-3-ol-17β-yl succinate 0.874 g of the product of Example 15 were dissolved in 30 ml of ethanol and the solution was added dropwise to a solution of 0.132 g of sodium bicarbonate in 30 ml of water. The ethanol was eliminated by azetropy and the aqueous solution was filtered on a Millipore ® membrane (0.45 microns), then lyophilized to obtain 0.908 g of the desired sodium salt with a specific rotation of $[\alpha]_D = +67° \pm 1.5°$ (c=1% in water) and a Rf=0.73 (thin layer chromatography; support: KC 18 Whatman ® eluant: mixture of methanol and aqueous 0.05 molar solution of ammonium acetate (80-20)).

EXAMPLE 17

11β-[4-(N-methyl-isopropylamino-phenyl]-17α-(1-propynyl)-Δ$^{4,9}$-estradien-3-one-17β-yl acid succinate A solution of 2.159 of 11β-[4-(N-methyl-isopropylaminophenyl]-17α-(1-propynyl)-Δ$^{4,9}$-estradien-17β-ol-3-one, 22 ml of triethylamine, 2.52 g of succinic anhydride, 8.1 ml of triethylamine and 1.07 g of 4-dimethylamino pyridine was refluxed for 24 hours. Another 0.339 g of succinic anhydride were added and reflux was continued for 74 hours. After cooling, the reaction medium was poured into 36 ml of 2N hydrochloric acid and the pH was adjusted to 6 by addition of sodium acetate. After decantation of the organic phase, the aqueous phase was re-extracted with chloroform. The combined chloroform phases were washed with water, dried on sodium sulfate and evaporated to dryness under vacuum. The residue was chromatographed on a column of 300 g of Kieselgel 60 ® silica, eluting first with ethyl ether and then with ethyl ether with 3% acetic acid to obtain 1.493 g of crude product which was crystallized from a methylene chloride - ethyl ether mixture to obtain 1.082 g of the sought acid succinate with a melting point of approx. 155° C. and a Rf=0.47 (thin layer chromatography; support: KC 18 Whatman ® eluant: mixture of methanol and aqueous 0.05 molar solution of ammonium acetate (80-20)).

EXAMPLE 18

Sodium and 11β-[4(N-methyl-isopropylamino)-phenyl]-17α-(1-propynyl)-Δ$^{4,9}$-estradien-3-one-17β-yl succinate Using the procedure of Example 16, 0.128 g of sodium bicarbonate in 30 ml of water and 0.933 g of the product of Example 17 in 30 ml of ethanol were reacted to obtain 0.915 g of the sought sodium salt with a specific rotation of $[\alpha]_D = +40.5° \pm 1.5°$ (c=1% in water) and a Rf=0.47 (thin layer chromatography, support KC 18 Whatman ®; eluant: mixture of methanol and aqueous 0.05 molar solution of ammonium acetate (80-20)).

EXAMPLE 19

Tablets were prepared containing 50 mg of the Product of Example 10 and sufficient excipient of talc, starch and magnesium stearate for a tablet weighing 120 mg.

EXAMPLE 20

A collyrium was prepared containing 2 g of the Product of Example 10 and sufficient, Excipient of distilled water, sodium chloride, methyl cellulose, sodium borate) for a volume of 100 ml.

PHARMACOLOGICAL STUDY

1) Measurement of the relative bond affinity for the receptors of steroid hormones:

Glucocorticoid receptor of rat's thymus:

Male rats weighing 160 to 200 g were suprarenalectomized and 4 to 8 days after this removal, the animals were killed. The thymuses were removed and homogenized at 0° C. using a Potter teflon-flask in a (TSD) 10 Mm Tris, 0.25M saccharose, 2 mM dithiothreitol, HCl pH 7.4 buffer (1 g of tissue per 10 ml of TSD). The homogenate was then ultracentrifuged at 105,000 g×90 mn at 0° C. Aliquots of the supernatant "cytosol", were incubated at 0° C. for 4 hours and 24 hours with a constant concentration (T=2.5 nM) of tritiated dexamethasone in the presence of increasing concentrations (0-2,500 nM) of cold dexamethasone or of the cold product under test. The concentration of the bonded tritiated dexamethasone (B) was then measured in each incubate by the technique of adsorption with carbon-dextran.

Progesterone receptor of rabbit's uterus:

Impuberal female rabbits weighing about 1 kg received a cutaneous application of 25 ug of estradiol and five days after this treatment, the animals were killed and the uteruses were removed, weighed and homogenized at 0° C. using a Potter teflon-flask in a (TS) 10 mM Tris, 0.25M saccharose, HCl pH 7.4 buffer (1 g of tissue per 50 ml of TS). The homogenate was then ultra-centrifuged (105,000 g×90 mn) at 0° C. Aliquots of the supernatant, "cytosol", were incubated at 0° C. for 2 hours and 24 hours with a constant concentration (T=5 nm) of tritiated R 5020 (17,21-dimethyl-19-nor- 4,9-pregnadien-3,20-dione), strongly progestomimetic having a great affinity for the progesterone receptor, in the presence of increasing concentrations (0-2500 nM) of cold progesterone, or of the product under test. The concentration of bonded tritiated R 5020 (B) was then measured in each incubate by the technique of adsorption with carbon-dextran.

Androgen receptor of rat's prostate

Male rats weighing 160 to 200 g were castrated and 24 hours after the castration, the animals were killed. The prostates were removed, weighed and homogenized at 0° C. using a Potter teflon-flask in a (TSDPM) 10 mM Tris, 0.25M saccharose, 0.1 nM phenylmethanesulfonylfluoride, 20 mM molybdate, 2 mM dithiothreitol, HCl pH 7.4 buffer (1 g of tissue per 5 ml of TSDPM). The homogenate was ultracentrifuged (105,000 g×60 mn) at 0° C. and aliquots of the supernatant "cytosol", were incubated at 0° C. with a constant concentration in the presence of increasing concentrations (0-1000 nM) of cold testosterone or of the product under test. After half an hour and 24 hours of incubation, the concentration of bonded tritiated testosterone (B) was measured in each incubate by the technique of adsorption with carbon-dextran.

Calculation of the relative bond affinity:

The calculation of the relative bond affinity (RBA) was identical for all receptors. The following two curves were drawn: the percentage of bonded tritiated hormone B/T as a function of the logarithm of the concentration of the cold reference hormone and B/T as a function of the logarithm of the concentration of the cold product under test. The straight line of the equation:

$$I_{50} = (B\ max + B/T\ min)/2$$

was determined.

B max = Percentage of bonded tritiated hormone for an incubation of this tritiated hormone at the concentration (T).

B min = Percentage of bonded tritiated hormone for an incubation of this tritiated hormone at the concentration (T) in the presence of a great excess of cold hormone ($2500 \times 10^{-9}$M).

The intersections of the straight line $I_{50}$ and the curves allowed the evaluation of the concentrations of the cold reference hormone (CH) and of the cold product under test (CX) which inhibited by 50% the bonding of the tritiated hormone on the receptor. The relative bond affinity (RBA) of the product under test was determined by the equation RBA=100 (CH)/(CX)

The results obtained are the following:

| Examples | Progesterone 2H | 24H | Glucocorticoid 4H | 24H | Androgen 0,5H | 5H |
|---|---|---|---|---|---|---|
| EX. 5 | 2 | 8 | 28 | 77 | 0,6 | 1 |
| EX. 12 | 1,2 | 3,6 | 9,5 | 24 | 0,8 | 0,3 |
| EX. 4 | 14 | 26 | 31,5 | 27 | 5,1 | 2,8 |
| EX. 2 | 21 | 88 | 62 | 48 | 12 | 39 |
| EX. 10 | 3 | 13 | 37 | 77 | 1,9 | 8,6 |
| EX. 6 | 2 | 6 | 26 | 54 | 2,2 | 4,1 |

The products of Examples 12 and 10 showed a good antiprogesterone activity.

2) Anti-glucocorticoid activity vis-a-vis dexamethasone
    Study in vitro
    Incorporation of uridine in rat thymocytes Glucocorticoids cause an inhibition of the incorporation of nucleosides in lymphoid tissue and the measurement of the incorporation of radio-active uridine in the thymocytes in the presence of a product under test allow its glucocorticoid activity to be evaluated.

Method

It was in accordance with the technique described by Dausse et al (3). The thymus of a suprarenalectomized rat weighing 160 to 180 g was removed, shredded and homogenized slowly using a teflon-flask homogenizer in Hanks solution. The cellular suspension obtained was filtered on gauze and then centrifuged at 800 g×10 mn. A new centrifugation was then carried out at 800 g×10 mn. The deposit was suspended in a nutritive medium (M.E.M. Gibco) and the cellular concentration was adjusted to approximately $20 \times 10^6$ cells per ml. Aliquots of 250 ul were then incubated under carbogen for 3 hours at 37° C. with $5 \times 10^{-8}$M of dexamethasone in the presence or not of increasing concentrations of product ($10^{-8}$M to $10^{-6}$M). 0.1 uCi of tritiated uridine was then added to each incubate and the incubation was continued for one hour. The incubates were then cooled and 1 ml of a cold solution of trichloracetic acid (TCA) at 5% weight/volume was added. The precipitates were collected on Whatman GF/C filters and were washed with 4×2 ml of 5% iced TCA. The radioactivity retained on the filters (representing the tritiated uridine incorporated in the thymocytes) was measured using a liquid scintillation spectrometer.

| Product of Example | Thymocytes % of inhibition of the incorporation of uridine Molar concentration of the product under test | | |
|---|---|---|---|
| | $10^{-6}$M | $10^{-7}$M | $10^{-8}$M |
| 5 | 135 | 100 | 28 |
| 12 | 104 | 62 | 8 |
| 4 | 22 | 2,5 | 0 |
| 2 | 68 | 1 | 0 |
| 10 | 78 | 19 | 0 |
| 6 | 78 | 27 | 0 |

The products of Examples 5 and 12 showed a good antiglucocorticoid activity.

Various modifications of the products and method of the invention may be made without departing from the spirit or scope thereof and it should be understood that the invention is intended to be limited only as defined in the appended claims.

What we claim is:
1. A compound of the formula

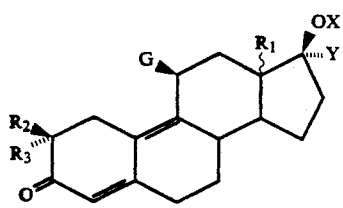

wherein $R_1$ is an aliphatic hydrocarbon of 1 to 8 carbon atoms, $R_2$ and R are individually hydrogen or alkyl of 1 to 4 carbon atoms, G is phenyl optionally substituted with at least one member of the group consisting of alkyl, alkoxy and alkylthio of 1 to 4 carbon atoms, halogen, —OH, —CF₃, alkylsulfoxide, alkylsulfonyl, —NH₂, mono- and dialkylamino of 1 to 4 carbon atoms and acyl and linked to the steroid nucleus by a carbon atom, X is $X_A$ or $X_B$, $X_A$ is selected from the group consisting of hydrogen, alkyl of 1 to 8 carbon atoms, aralkyl of 7 to 15 carbon atoms, acyl of an organic carboxylic acid of 1 to 8 carbon atoms and Y is -B-O—CO—A-Z, B is a saturated or unsaturated, linear or branched alkylene of 1 to 8 carbon atoms, A is a saturated or unsaturated, linear or branched alkylene of 1 to 6 carbon atoms and optionally interrupted or ended by a bivalent aromatic or is a bivalent aromatic and Z is —COOH or —SO₃H which may be salified with an alkali metal, alkaline earth metal, an organic amine or —NH₄ or $X_B$ is —COAZ, A and Z are defined as above and Y is selected from the group consisting of —C≡—R₄, —CH═CH—R₄ and —CH₂—CH₂—R₄, R₄ is selected from the group consisting of hydrogen, halogen, alkyl of 1 to 6 carbon atoms, trialkylsilyl having 3 to 12 carbon atoms and phenyl, the alkyl and phenyl being optionally substituted and the 13-wavy line indicated that $R_1$ can be in the α- or β-position.

2. A compound of claim 1 having the formula

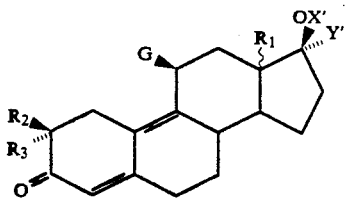

wherein either X' is hydrogen and Y' is $Y'_A$, $Y'_A$ being

in which B' is one of —CH═CH—CH₂— or —C≡C—CH₂—, A' is —(CH₂)ₙ— in which n is two to six or an ortho-, meta- or para- phenylene and Z' is carboxy or sulfo functions or their sodium salt, or X' is $X'_B$, $X'_B$ being

in which n and Z' are as defined previously and Y' is $Y'_B$, $Y'_B$ being —C≡C—R'₄ or —CH═CH—R'₄ in which R'₄ is hydrogen, halogen, trimethylsilyl, or methyl optionally substituted by one or more halogen, hydroxy or alkoxy, alkylthio or alkylamino of one to four carbon atoms, dialkylamino of two to eight carbon atoms or trialkylsilyl of three to twelve carbon atoms.

3. A compound of claim 1 wherein $R_1$ is 13β-methyl and $R_2$ and $R_3$ are hydrogen.

4. A compound of claim 1 which is sodium and 21-chloro-11β-[-4-dimethylamino-phenyl]-19-nor-17α-Δ⁴,⁹-pregnadien-3-one 20-yn-17β-yl succinate or sodium and 11β-[4-methylthio-phenyl]-17α-(1-propynyl-Δ⁴,⁹-estradien-3-one-17β-yl succinate or 1(β-[4-dimethylamino-phenyl]-17α-(1-propynyl)-Δ⁴,⁹-estradien-3-one-17β-yl acid succinate and its sodium salt.

5. A compound having a formula selected from the group consisting of

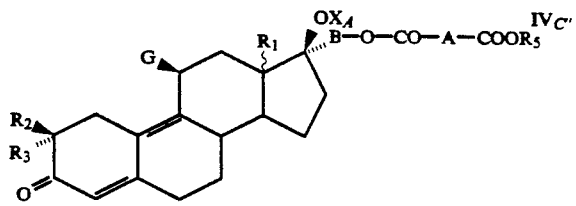

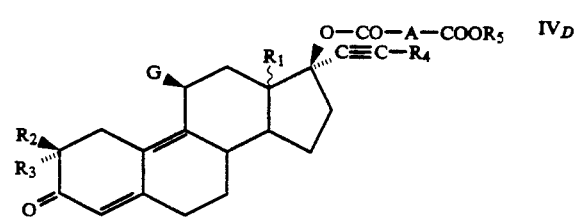

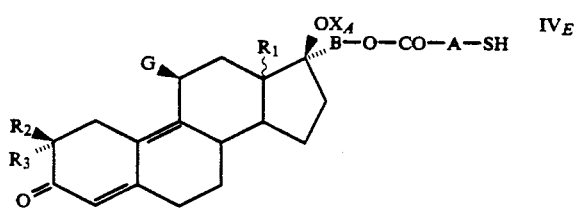

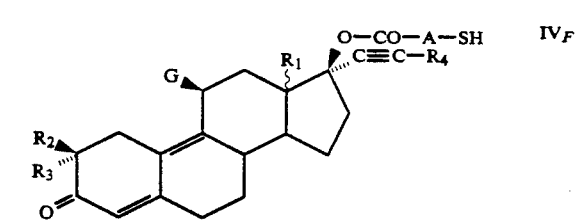

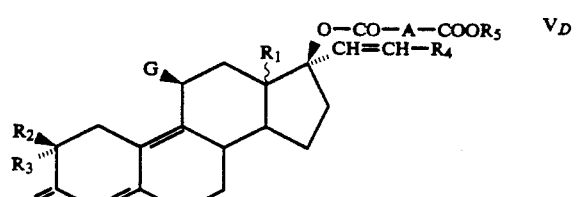

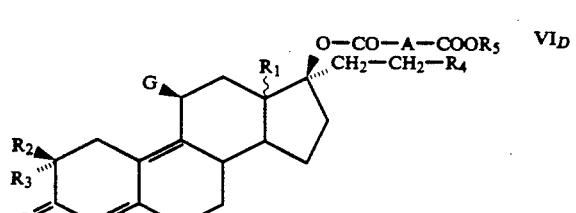

wherein $R_1$, $R_2$, $R_3$, $R_4$, A, B, $X_A$, G and the wavy line have the definition of claim 1 and $R_5$ is alkyl of 1 to 6 carbon atoms or aralkyl of 7 to 12 carbon atoms.

6. An antiglucocorticoid and antiprogestomimetic composition comprising an antiglucocorticoidally and antiprogestomimetically effective amount of at least one compound of claim 1 and an inert pharmaceutical carrier.

7. A composition of claim 6 comprising an effective amount of at least one compound of claim 2.

8. A composition of claim 6 wherein the active compound is selected from the group consisting of sodium and 21-chloro-11β-[4-dimethylamino-phenyl]-19-nor-17α-Δ$^{4,9}$-pregnadien-3-one 20-yn-17β-yl succinate or sodium and 11β-[4-methylthio-phenyl]-17α-(1-propynyl)-Δ$^{4,9}$-estradien-3-one-17β-yl succinate or 11β-[4-dimethylamino-phenyl]-17α-(1-propynyl)-Δ$^{4,9}$-estradien-3-one-17β-yl acid succinate and its sodium salt.

9. A method of inducing antiglucocorticoid and antiprogestomimetic activity in warm-blooded animals comprising administering to warm-blooded animals an antiglucocorticoidally and antiprogestomimetically effective amount of at least one compound of claim 1.

10. A method of claim 9 comprising administering to warm blooded animals an effective amount of at least one compound of the formula

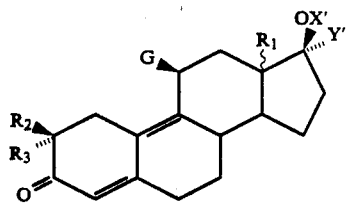

wherein either X' is hydrogen and Y' is Y'$_A$, Y'$_A$ being

-B'-O-CO-A'-Z' in which B' is one of —CH=CH—CH$_2$— or —C≡C—CH$_2$—, A' is —(CH$_2$)$_n$— in which n is two to six or an ortho-, meta- or para- phenylene and Z' is carboxy or sulfo functions or their sodium slat, or X' is X'$_B$, X'$_B$ being —CO—(CH$_2$)$_n$—Z' in which n and Z' are as defined previously and Y' is Y'$_B$, Y'$_B$ being —C≡C—R'$_4$ or —CH=CH—R'$_4$ in which R'$_4$ is hydrogen, halogen, trimethylsilyl, or methyl optionally substituted by one or more halogen, hydroxy or alkoxy, alkylthio or alkylamino of one to four carbon atoms, dialkylamino of two to eight carbon atoms or trialkylsilyl of three to twelve carbon atoms.

11. A method of claim 9 wherein the active compound is selected from the group consisting of sodium and 21-chloro-11β-[4-dimethylamino-phenyl]-19-nor-17α-Δ$^{4,9}$-pregnadien-3-one 20-yn-17β-yl succinate or sodium and 11β-[4-methylthio-phenyl]-17α-(1-propynyl)-Δ$^{4,9}$-estradien-3-one-17β-yl succinate or 11β-[4-dimethylamino-phenyl]-17α-(1-propynyl)-Δ$^{4,9}$-estradien-3one-17β-yl acid succinate and its sodium salt.

12. A compound of claim 1 wherein G is phenyl substituted in position 4 by a member selected from the group consisting of amino, methylamino, dimethylamino, dipropylamino, N-methyl ethylamino, N-methyl isopropylamino, N-methyl isobutylamino, formyl, acetyl, methoxy, methylthio, ethylthio, isopentylthio, methyl, isopropyl, fluorine, chlorine and bromine.

* * * * *